United States Patent
Hattori et al.

(10) Patent No.: US 7,732,482 B2
(45) Date of Patent: *Jun. 8, 2010

(54) **COMPOUND FROM *ANTRODIA CAMPHORATA* AND THE USE THEREOF**

(75) Inventors: Masao Hattori, Sugitani Toyama (JP); Chia-Chin Sheu, Taoyuan County (TW); Coolin Yang, Jaili Township, Tainan County (TW)

(73) Assignee: Simpson Biotech Co., Ltd., Taoyuan County (TW)

( * ) Notice: Subject to any disclaimer, the term of this patent is extended or adjusted under 35 U.S.C. 154(b) by 4 days.

This patent is subject to a terminal disclaimer.

(21) Appl. No.: 12/153,405

(22) Filed: May 19, 2008

(65) Prior Publication Data
US 2009/0048330 A1 Feb. 19, 2009

Related U.S. Application Data

(63) Continuation of application No. 11/204,392, filed on Aug. 16, 2005, now abandoned.

(30) Foreign Application Priority Data

Aug. 17, 2004 (EP) .................................. 04254939

(51) Int. Cl.
*A61K 31/4015* (2006.01)
*C07D 207/444* (2006.01)
*C07D 207/46* (2006.01)
*A61K 31/341* (2006.01)
*C07D 307/60* (2006.01)

(52) U.S. Cl. ............... 514/425; 548/548; 548/545; 548/542; 514/473; 549/233; 549/253

(58) Field of Classification Search ................ 514/545, 514/548, 425, 473; 548/425, 545, 548, 542; 549/233, 253
See application file for complete search history.

(56) References Cited

U.S. PATENT DOCUMENTS 7,432,288 B2 * 10/2008 Bostrom et al. ............. 514/343

OTHER PUBLICATIONS

Byrn et al. Solid-State Chemistry of Drugs, 2d, Chapter 11 Hydrates and Solvates, 233-247, 233.*
A.M. Rouhi, Chem. & Eng. News, Feb. 24, 2003, 81(8), 32-35.*
Morissette et al. Adv. Drug Delivery Rev. 2004, 56, 275-300.*
Strieter et al. Chest 2009, 136, 1364-1370.*
Gunay-Aygun et al. from GeneReviews, R.A. Pagon (Ed.), University of Washington (Pub.), 2008.*
P. Libby Nutrition Reviews 2007, 65(12), S140-S146.*
Chen et al. Journal of Agriculture and Food Chemistry 2008, 56, 7017-7022.*

* cited by examiner

*Primary Examiner*—Rebecca L Anderson
*Assistant Examiner*—Jason M Nolan
(74) *Attorney, Agent, or Firm*—WPAT, P.C.; Anthony King

(57) ABSTRACT

The present invention relates to novel compounds from *Antrodia camphorata* and the use thereof.

24 Claims, 12 Drawing Sheets

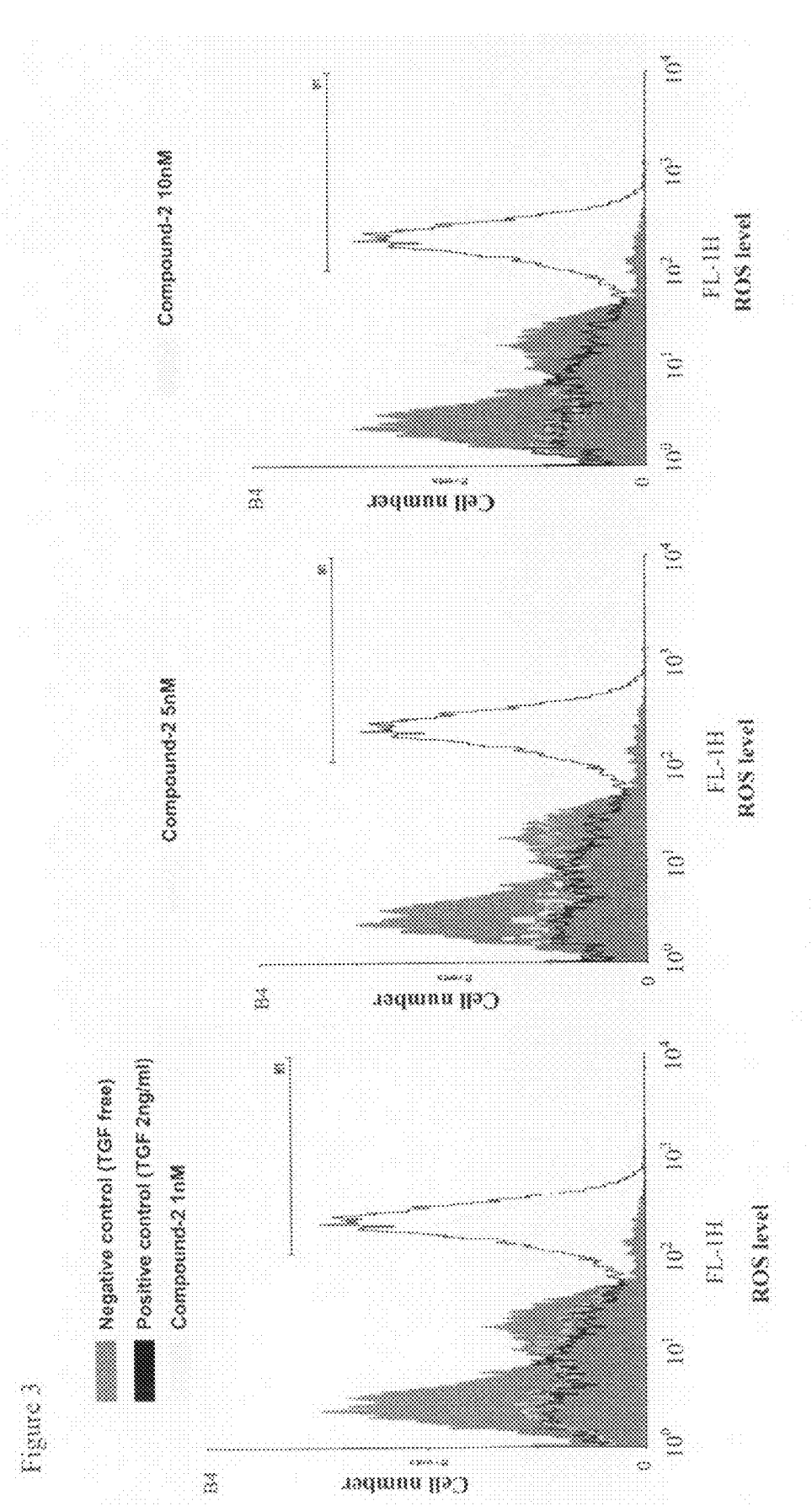

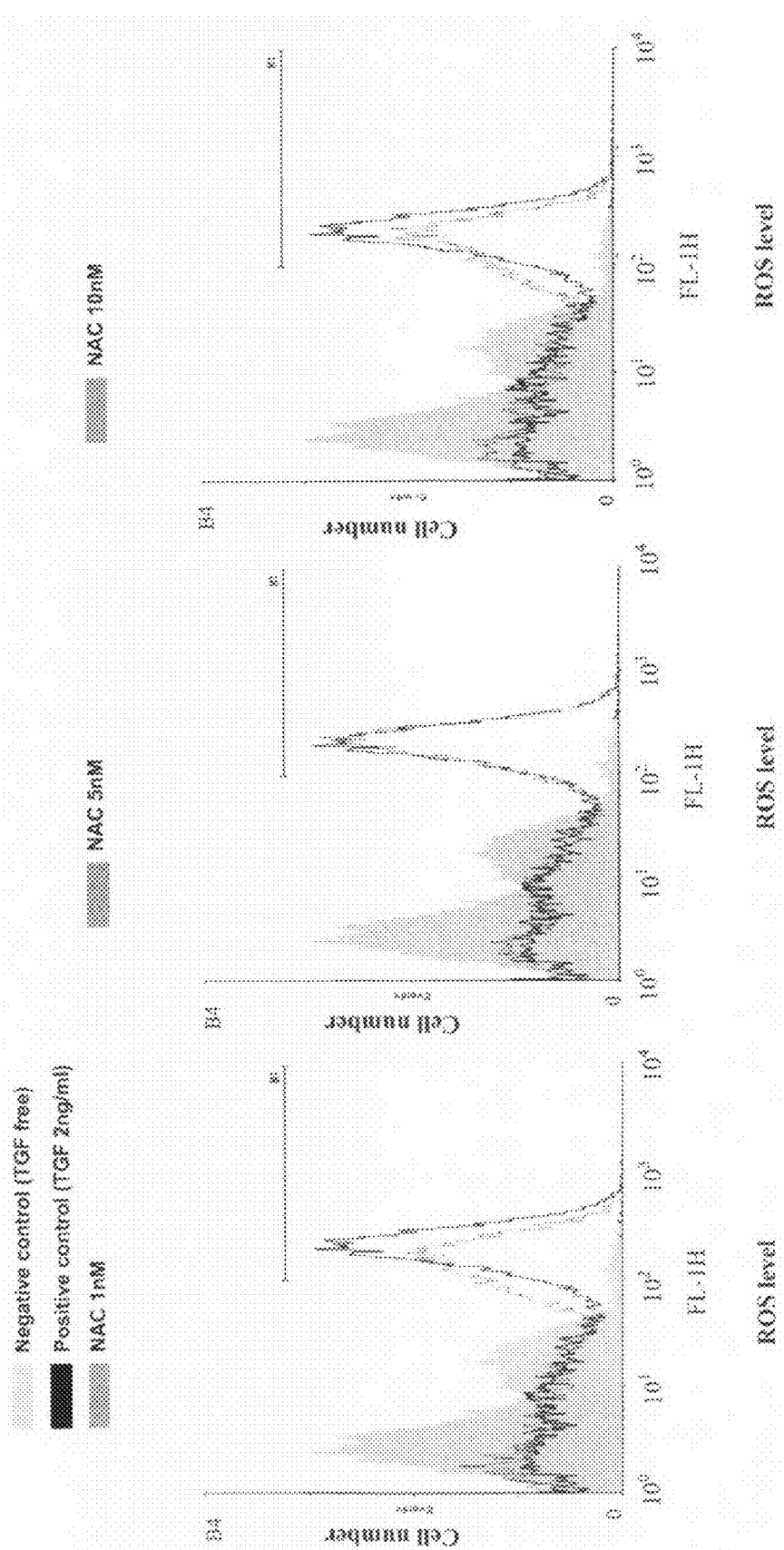

(A) Negative control (TGF-β free). (B) Positive control (TGF-β 2ng/ml)
(C) compound-2 1μg/kg.

*Collagen fiber accumulation in the sinusoidal wall was blue-stained (arrows).
original magnification x200

COMPOUND FROM *ANTRODIA CAMPHORATA* AND THE USE THEREOF

PRIORITY STATEMENT

This application is a continuation of application Ser. No. 11/204,392 filed on Aug. 16, 2005 now abandoned, and from which priority is claimed under 35 U.S.C. §120. The entire contents of which are incorporated herein by reference. Further, a claim of priority under 35 U.S.C. §119 is made to European Patent Application 04254939.4 filed on Aug. 17, 2004, the entire contents of which are hereby incorporated by reference.

FIELD OF THE INVENTION

The present invention relates to novel compounds from *Antrodia camphorata* and the use thereof. The present invention relates to the composition comprising the compounds of the invention.

BACKGROUND OF THE INVENTION

The fruiting body of *Antrodia camphorata* (Polyporaceae, Aphyllophorales) is well known in Taiwan as a traditional Chinese medicine. It grows only on the inner heartwood wall of the endemic evergreen *Cinnamomun kanehirai* (Hay)(Lauraceae) in Taiwan. It is rare and has not been cultivated. The fruiting bodies have been used for treating of food and drug intoxication, diarrhea, abdominal pain, hypertension, itchy skin, and liver cancer. Very few biological activity studies have been reported hitherto.

*Antrodia camphorata*, also known as "niu-chang-chih" or "niu-chang-ku" in Taiwan, was recently reported as a new fungus species characterized by the cylindrical shape of its basidiospores appearing in fruiting bodies, weakly amyloid skeletal hyphae, bitter taste and light cinnamon resupinate to pileate basidiocarps, as well as chlamydospores and anthroconidia in pure culture. The growth of this new fungus species is extremely slow and restricted to an endemic tree species, *Cinnamomum kanehirai* Hay (Lauraceae), as the only host. The detailed characterization and taxonomic position of *Antrodia camphorata* were described in Wu, S.-H., et al., *Antrodia cinnamomea* ("niu-chang-chih"), New combination of a medicinal fungus in Taiwan, *Bot. Bull. Acad. Sin.* 38: 273-275 (1997).

In Taiwanese folk medicine, the fruiting bodies of *Antrodia camphorata* are believed to have certain medical effects. According to the traditional way, the fruiting bodies are ground into dry powder or stewed with other herbal drugs for oral uptake to treat conditions caused by poisoning, diarrhea, abdominal pain, hypertension, skin itches and liver cancer. However, few pharmacological or clinical studies in these aspects have appeared in literature to date. Because of the stringent host specificity and rarity in nature, as well as the failure of artificial cultivation, "niu-chang-chih" is very expensive in Taiwan. In recent years, the fruiting bodies of this fungus with high quality have been sold at an extremely high price of around U.S.$ 15,000 per kg.

Oxidative stress including the generation of reactive oxygen species (ROS) can be implicated as a cause of hepatic fibrosis (M. Chojkier et al., Stimulation of collagen gene expression by ascorbic acid in cultured human fibroblasts, A role for lipid peroxidation, *J. Biol. Chem.* 264 (1989), pp. 16957-16962. and I. Shimizu, Antifibrogenic therapies in chronic HCV infection. *Curr Drug Targets Infect Disord* 1 (2001), pp. 227-240). It has been reported that hepatocytes, which are undergoing oxidative stress, release ROS that stimulate hepatic stellate cell (HSC) proliferation and transformation into α smooth muscle actin (α-SMA)-positive myofibroblast-like cells (G. S. Baroni et al., Fibrogenic effect of oxidative stress on rat hepatic stellate cells, *Hepatology* 27 (1998), pp. 720-726). These HSCs are referred to as activated cells and are responsible for the abnormal extracellular matrix (ECM) proteins during hepatic fibrosis to cirrhosis. Transforming growth factor-β (TGF-β) is a major fibrogenic cytokine, regulating the production, degradation, and accumulation of ECM proteins in hepatic fibrogenesis (A. Casini et al., Regulation of extracellular matrix synthesis by transforming growth factor β1 in human fat-storing cells, *Gastroenterology* 105 (1993), pp. 245-253). This cytokine induces its own expression in activated HSCs, thereby creating a self-perpetuating cycle of events, referred to as an autocrine loop. TGF-β gene expression correlates with the extent of hepatic fibrosis (A. Castilla et al., Transforming growth factors β1 and α in chronic liver disease. Effects of interferon α therapy. *N. Eng. J. Med.* 324 (1991), pp. 933-940.), and an increased production of ROS such as $H_2O_2$ in fibrotic livers is associated with the up-regulation of TGF-β (E. R. Garcia-Trevijano et al., Transforming growth factor β1 induces the expression of α1(I) procollagen mRNA by a hydrogen peroxide-C/EBP β-dependent mechanism in rat hepatic stellate cells, *Hepatology* 29 (1999), pp. 960-970).

Fibrotic diseases are characterized by excessive scarring due to excessive production, deposition, and contraction of extracellular matrix. This process usually occurs over many months and years, and can lead to organ dysfunction or death. Examples of fibrotic diseases include diabetic nephropathy, liver cirrhosis, idiopathic pulmonary fibrosis, rheumatoid arthritis, fibrosarcomas, arteriosclerosis, and scleroderma (systemic sclerosis; SSc). Fibrotic disease represents one of the largest groups of disorders or which there is no effective therapy and thus represents a major unmet medical need. Often the only redress for patients with fibrosis is organ transplantation; since the supply of organs is insufficient to meet the demand, patients often die while waiting to receive suitable organs.

Oxidative stress is associated with liver fibrosis and activation of hepatic stellate cells either directly or through paracrin stimulation by injured hepatocytes. Factors increasing reactive oxygen species (ROS) generation may also be involved in stimulation of excessive matrix production in vivo. Increase in hydrogen peroxide production leads to activation of a potent profibrogenic mediator TGF-β, supporting the idea that oxidative stress has important roles in fibrogenesis (Mehmet R. M., et al., The effect of taurine treatment on oxidative stress in experimental liver fibrosis, *Hepatology Research*, 28, 207-215 (2004).

TGF-β induces fibroblasts to synthesize and contract ECM, this cytokine has long been believed to be a central mediator of the fibrotic response TGF-β1 triggered enhancement of α-SMA and collagen type I expression.

The discovery in 1987 that nitric oxide (NO) accounted for the bioactivity of endothelium-derived relaxing factor rapidly led to an explosion of information on the physiological and pathological roles of this molecule. Although most well known for its physiological roles in vasorelaxation, neurotransmission, inhibition of platelet aggregation, and immune defense, NO also acts as an intracellular messenger for various cells in almost every system in the body (Peeyush and Chandan, *Lancet Oncol* 3:149, 2001).

Nitric oxide, this highly reactive free radical agent is synthesized from L-arginine by nitric oxide synthase. It acts in both the intercellular and extracellular environment and is believed to be a regulatory molecule in a variety of soft tissues including articular cartilage, ligament, tendon, skeletal muscle and bone. It is induced during tendon healing in vitro.

It appears that there is a dose-dependent effect upon its contribution to fibroblast production of collagen. There is also a site-specific effect with the anterior cruciate ligament-derived fibroblasts capable of producing more nitric oxide than from cells derived from the medial collateral ligament. Manipulation of nitric oxide production has been thought to help accelerate repetitive overuse tendon injury and tendinosis. The role of nitric oxide in the incorporation of an ACL graft remains under investigation through studies using transfection of cDNA for nitric oxide synthase (Deehan et al., *J Bone Joint Surg* 87(7):889, 2005).

Nitric oxide (NO) is integral to many biological processes including the control of blood pressure, protection against microbial infection and neurotransmission. Additionally, it appears to be a potent cytotoxin to tumor cells. Among its mechanisms of action on malignant cells, nitric oxide appears to inhibit DNA synthesis and mitochondrial respiration in vitro. It induces programmed cell death or apoptosis in these cells. Unfortunately, NO itself is difficult to administer as it is a highly reactive gas. It also causes hypotension if administered systemically. These limitations have prevented its use to date as an antineoplastic agent.

Generation of nitric oxide (NO) by inducible nitric oxide synthase (iNOS) is a cardinal feature of inflamed tissues including those of the gastrointestinal tract. iNOS overexpression with high levels of NO generation provides a plausible link between inflammation and cancer initiation, progression, and promotion. NO is involved in a number of biological actions including cytotoxicity of phagocytic cells and cell-to-cell communication in the central nervous system. NO is also involved in the immune response (inducible NOS or iNOS), smooth muscle relaxation (endothelial NOS or eNOS), and neuronal signaling (neuronal NOS or nNOS).

Treatment of overuse tendinopathy using transdermal nitric oxide-generating agents is disclosed in U.S. Patent Application Pub. No. 2005171199. Use of nitric oxide scavengers to treat side effects caused by therapeutic administration of sources of nitric oxide is disclosed in U.S. Pat. No. 6,596,733. Use of products that release nitric oxide in vivo to treat or prevent infectious diseases in humans or animals is described in Germany patent application Pub. No. DE10303196 A1. Nitric oxide (NO) synthase inhibitor to treat or prevent Type II diabetes is described in Australia patent application Pub. No. AU4865800 A. Use of nitric oxide-releasing agents to treat impotency is disclosed in U.S. Pat. No. 6,290,981. Modification of nitric oxide activity to treat fas-induced pathologies is mentioned in PCT publication no. WO9903462 A1. Combined use of angiotensin inhibitors and nitric oxide stimulators to treat fibrosis is described in U.S. Pat. No. 6,139,847 A. Blocking induction of tetrahydrobiopterin to block induction of nitric oxide synthesis is disclosed in U.S. Pat. No. 6,274,581.

SUMMARY OF THE INVENTION

This invention provides a compound having the formula

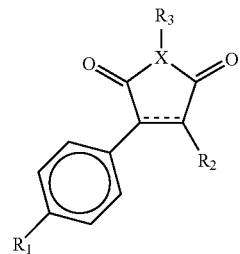

its tautomeric forms, its stereoisomers, its polymorphs, its pharmaceutically acceptable salts, or its pharmaceutically acceptable solvates, wherein X is N or O; $R_1$ is H, hydroxyl, $C_{1-10}$ alkyloxy, $C_{2-10}$ alkenyloxy, or $C_{2-10}$ alkynyloxy; $R_2$ is H, hydroxyl, $C_{1-10}$ alkyl, $C_{2-10}$ alkenyl or $C_{2-10}$ alkynyl; $R_3$ is $C_{1-10}$ alkyl, $C_{2-10}$ alkenyl or $C_{2-10}$ alkynyl; ═══ denotes a single or double bond; provided that if ─── denotes a single bond, the compound has the formula:

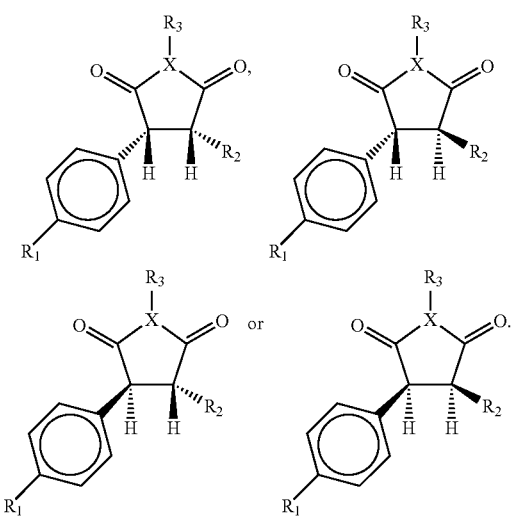

This invention also provides a mixture from *Antrodia camphorate*, which is prepared from water or organic solvent extract of mycelium of *Antrodia camphorate*.

This invention further provides a composition comprising a compound having the formula

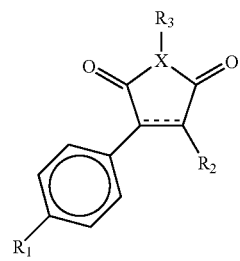

its tautomeric forms, its stereoisomers, its polymorphs, its pharmaceutically acceptable salts, or its pharmaceutically acceptable solvates, wherein X is N or O; $R_1$ is H, hydroxyl, $C_{1-10}$ alkyloxy, $C_{2-10}$ alkenyloxy, or $C_{2-10}$ alkynyloxy; $R_2$ is H, hydroxyl, $C_{1-10}$ alkyl, $C_{2-10}$ alkenyl or $C_{2-10}$ alkynyl; $R_3$ is absent, H, hydroxyl or $C_{1-10}$ alkyl, $C_{2-10}$ alkenyl or $C_{2-10}$ alkynyl; $\overline{\phantom{==}}$ denotes a single or double bond; provided that if X is O, $R_3$ is absent; if $\overline{\phantom{==}}$ denotes a single bond, the compound has the formula:

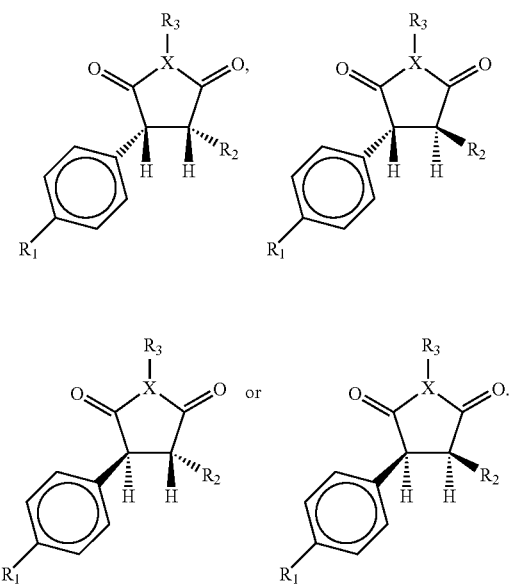

BRIEF DESCRIPTION OF THE DRAWINGS

FIG. 3 shows the flow cytometry results for ROS assay.

DETAILED DESCRIPTION OF THE INVENTION

Figure 1:
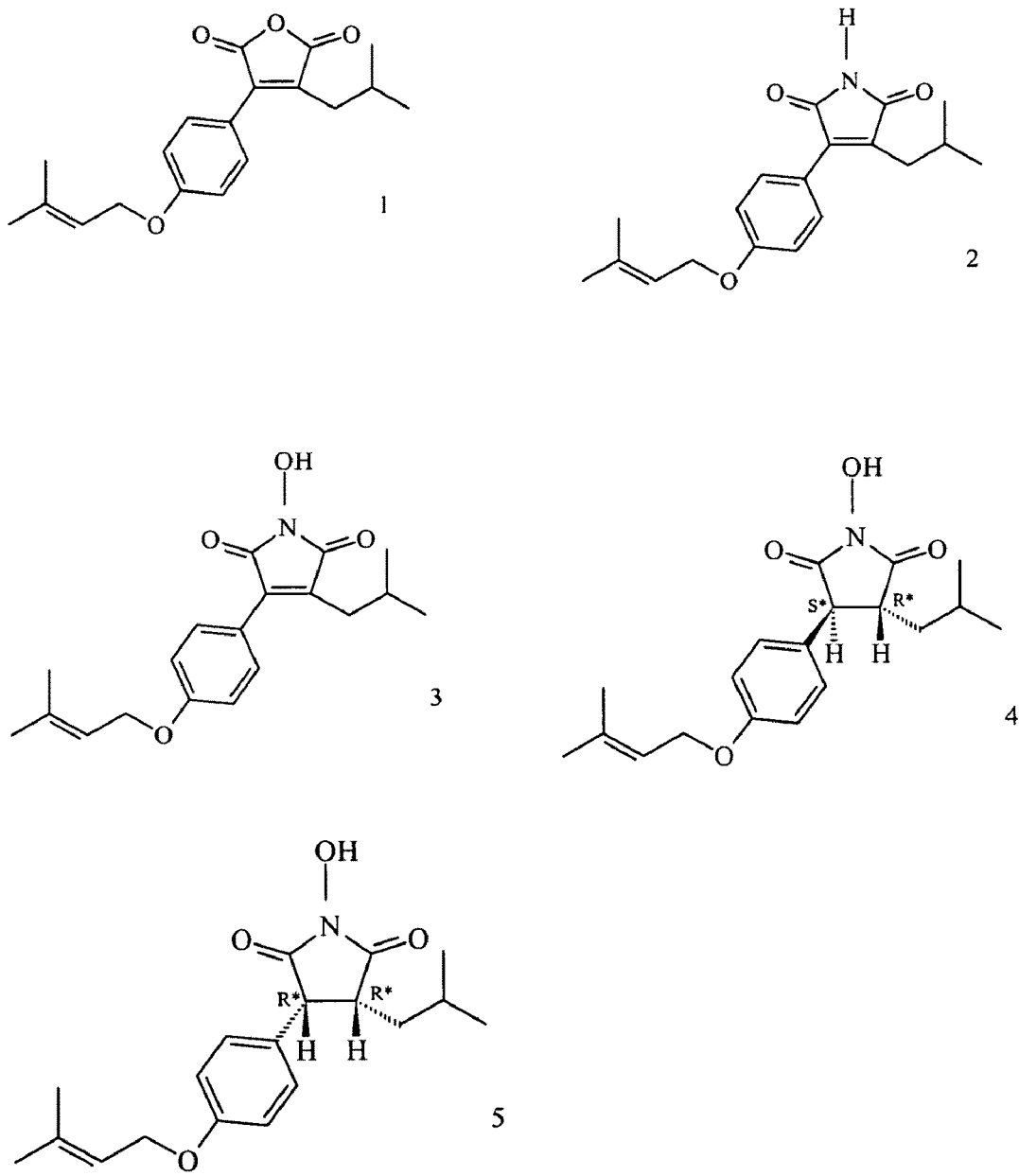
FIG. 1 shows the compounds 1-5 used in the present invention.

The present invention provides a compound having the formula

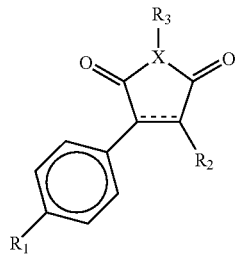

its tautomeric forms, its stereoisomers, its polymorphs, its pharmaceutically acceptable salts, or its pharmaceutically acceptable solvates, wherein X is N or O; $R_1$ is H, hydroxyl, $C_{1-10}$ alkyloxy, $C_{2-10}$ alkenyloxy, or $C_{2-10}$ alkynyloxy; $R_2$ is H, hydroxyl, $C_{1-10}$ alkyl, $C_{2-10}$ alkenyl or $C_{2-10}$ alkynyl; $R_3$ is $C_{1-10}$ alkyl, $C_{2-10}$ alkenyl or $C_{2-10}$ alkynyl; $\overline{\phantom{==}}$ denotes a single or double bond; provided that if $\overline{\phantom{==}}$ denotes a single bond, the compound has the formula:

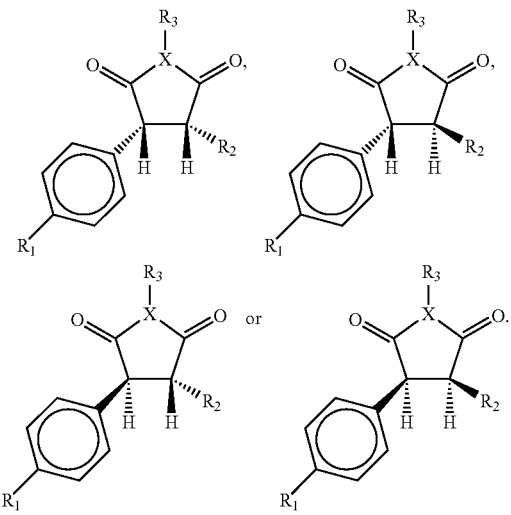

In the compound of the invention, the preferred $R_1$ is $C_{2-6}$ alkenyloxy, or $C_{2-6}$ alkynyloxy; the more preferred $R_1$ is $C_{2-6}$ alkenyloxy substituted with $C_{1-6}$ alkyl and the most preferred $R_1$ is butenyloxy substituted with methyl. In the compound of the invention, the preferred $R_2$ is $C_{1-6}$ alkyl, the most preferred $R_2$ is isobutyl.

Certain compounds may exist in one or more particular geometric, optical, enantiomeric, diasteriomeric, epimeric, stereoisomeric, tautomeric, conformational, or anomeric forms, including but not limited to, cis- and trans-forms; E- and Z-forms; c-, t-, and r-forms; endo- and exo-forms; R—, S—, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope- and halfchair-forms; and combinations thereof, hereinafter collectively referred to as "isomers" (or "isomeric forms").

If the compound is in crystalline form, it may exist in a number of different polymorphic forms.

The above exclusion does not pertain to tautomeric forms, for example, keto-, enol-, and enolate-forms, as in, for example, the following tautomeric pairs: keto/enol, imine/enamine, amide/imino alcohol, amidine/amidine, nitroso/oxime, thioketone/enethiol, N-nitroso/hyroxyazo, and nitro/aci-nitro.

Unless otherwise specified, the compounds of the present invention include all such isomeric forms, including (wholly or partially) racemic and other mixtures thereof. Methods for the preparation (e.g., asymmetric synthesis) and separation (e.g., fractional crystallization and chromatographic means) of such isomeric forms are either known in the art or are readily obtained by adapting the methods taught herein, or known methods, in a known manner.

Unless otherwise specified, the compounds of the present invention include also includes ionic, salt, solvate, and protected forms of thereof, for example, as discussed below.

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

The present invention also provides a mixture from mycelium of *Antrodia camphorata*, which comprises the compound of the invention. The mixture of the invention is prepared from water or organic solvent extract of mycelium of *Antrodia camphorata*. The organic solvent includes but is not limited to alcohol (such as $CH_3OH$, $C_2H_5OH$, $C_3H_7OH$), ester (such as acetyl acetate), alkane (such as hexane) and halogenated alkane (such as $CH_3Cl$, $C_2H_2Cl_2$). The preferred organic solvent is ethanol or alcoholic solvent without causing any side effect of human.

The mixture of the present invention inhibits factor increasing reactive oxygen species (ROS) generation. The mixture of the present invention also inhibits TGF-β mediated inflammation and fibrosis. The fibrosis is not limited but to include diabetic nephropathy, liver cirrhosis, idiopathic pulmonary fibrosis, rheumatoid arthritis, fibrosarcomas, arteriosclerosis, and scleroderma.

The mixture of the present invention also inhibits nitric oxide activities. The mixture can be used in treating or preventing of epithelial cell carcinogenesis and free radical damages.

Nitric oxide overproduction is associated with a wide range of disease states and/or indications, such as, for example, septic shock, ischemia, administration of cytokines, overexpression of cytokines, ulcers, inflammatory bowel disease (e.g., ulcerative colitis or Crohn's disease), diabetes, arthritis, asthma, Alzheimer's disease, Parkinson's disease, multiple sclerosis, cirrhosis, allograft rejection, encephalomyelitis, meningitis, pancreatitis, peritonitis, vasculitis, lymphocytic choriomeningitis, glomerulonephritis, uveitis, ileitis, liver inflammation, renal inflammation, hemorrhagic shock, anaphylactic shock, burn, infection (including bacterial, viral, fungal and parasitic infections), and the like.

Those of skill in the art recognize that the mixture described herein can be delivered in a variety of ways, such as, for example, orally, intravenously, subcutaneously, parenterally, rectally, by inhalation, and the like.

Since individual subjects may present a wide variation in severity of symptoms and each drug has its unique therapeutic characteristics, the precise mode of administration and dosage employed for each subject is left to the discretion of the practitioner.

Accordingly, the mixture of the present invention could be applied to treat or prevent septic shock, ischemia, overexpression of cytokines, ulcer, ulcerative colitis, diabetes, arthritis, asthma, Alzheimer's disease, Parkinson's disease, multiple sclerosis, cirrhosis, allograft rejection, encephalomyelitis, meningitis, pancreatitis, peritonitis, vasculitis, lymphocytic choriomeningitis, glomerulonephritis, uveitis, ileitis, liver inflammation, renal inflammation, hemorrhagic shock, anaphylactic shock, burn, Crohn's disease or infection.

The present invention also provides a composition, having the formula

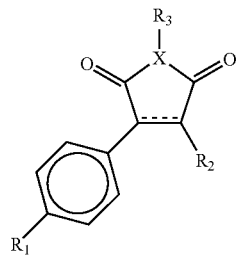

its tautomeric forms, its stereoisomers, its polymorphs, its pharmaceutically acceptable salts, or its pharmaceutically acceptable solvates, wherein X is N or O; $R_1$ is H, hydroxyl, $C_{1-10}$ alkyloxy, $C_{2-10}$ alkenyloxy, or $C_{2-10}$ alkynyloxy; $R_2$ is H, hydroxyl, $C_{1-10}$ alkyl, $C_{2-10}$ alkenyl or $C_{2-10}$ alkynyl; $R_3$ is absent, H, hydroxyl or $C_{1-10}$ alkyl, $C_{2-10}$ alkenyl or $C_{2-10}$ alkynyl; ⸺ denotes a single or double bond; provided that if X is O, $R_3$ is absent; if ⸺ denotes a single bond, the compound has the formula:

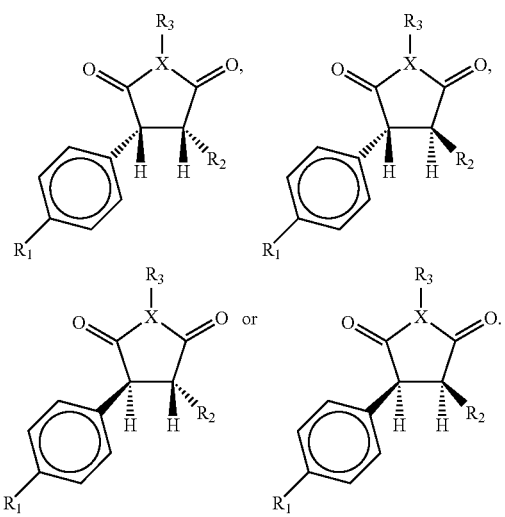

In the preferred embodiment, the compound is 3-isobutyl-4-[4-(3-methyl-2-butenyloxy)phenyl]furan-2,5-dione, 3-isobutyl-4-[4-(3-methyl-2-butenyloxy)phenyl]-1H-pyrrol-2,5-dione, 3-isobutyl-4-[4-(3-methyl-2-butenyloxy)phenyl]-1H-pyrrol-1-ol-2,5-dione, 3R*,4S*-1-hydroxy-3-isobutyl-4-[4-(3-methyl-2-butenyloxy)phenyl]pyrrolidine-2,5-dione, or 3R,4R*-1-hydroxy-3-isobutyl-4-[4-(3-methyl-2-buteny-loxy)phenyl]pyrrolidine-2,5-dione.

The composition inhibits factor increasing reactive oxygen species (ROS) generation. Further, the composition inhibits TGF-β mediated inflammation and fibrosis. The fibrosis is related to diabetic nephropathy, liver cirrhosis, idiopathic pulmonary fibrosis, rheumatoid arthritis, fibrosarcomas, arteriosclerosis, and scleroderma. The present composition can inhibit nitric oxide activities and can be for use in treating or preventing of epithelial cell carcinogenesis and free radical damages. In particular, the present composition could be applied to treat or prevent septic shock, ischemia, overexpression of cytokines, ulcer, ulcerative colitis, diabetes, arthritis, asthma, Alzheimer's disease, Parkinson's disease, multiple sclerosis, cirrhosis, allograft rejection, encephalomyelitis, meningitis, pancreatitis, peritonitis, vasculitis, lymphocytic choriomeningitis, glomerulonephritis, uveitis, ileitis, liver inflammation, renal inflammation, hemorrhagic shock, anaphylactic shock, burn, Crohn's disease or infection.

The compositions of the present invention can be used in the form of a solid, a solution, an emulsion, a dispersion, a micelle, a liposome, and the like, wherein the resulting composition contains one or more of the compounds of the present invention, as an active ingredient, in admixture with an organic or inorganic carrier or excipient suitable for enteral or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used.

The compositions of the invention may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing the active ingredient in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452 and 4,265,874, to form osmotic therapeutic tablets for controlled release.

In some cases, compositions for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example, peanut oil, liquid paraffin, or olive oil.

The compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Compounds contemplated for use in the practice of the present invention may also be administered in the form of suppositories for rectal administration of the drug. These compositions may be prepared by mixing the drug with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, it is up to the practitioner to determine a subject's response to treatment and vary the dosages accordingly.

EXAMPLES

The examples below are non-limiting and are merely representative of various aspects and features of the present invention.

Example 1

General Experimental Procedures

Melting points were measured on a Yanagimoto micro hot-stage melting point apparatus and uncorrected. Optical rotations were measured with a Jasco DIP-360 automatic polarimeter. UV spectra were measured with a Shimadzu UV-2200 recording spectrophotometer. IR spectra were measured with a Jasco FT/IR-230 infrared spectrometer. $^1$H- and $^{13}$C-NMR spectrum were measured with a Varian Unity Plus 500 spectrometer. EIMS and HR-EIMS were measured with a Jeol JMS-AX 505 HAD mass spectrometer at an ionization voltage of 70 eV. Column chromatography was carried out on silica gel BW-820 MH (normal phase) and Chromatorex-ODS DM1020T (reversed phase)(Fuji Silysia).

Extraction and Isolation

*Antrodia camphorata* mycelia powder (ACM)(60 g), from Simpson Biotech Co. Ltd., Taiwan, October 2001, were three times extracted with $CHCl_3$ for 3 h under reflux. The $CHCl_3$ extract (5.3 g) was chromatographed on silica gel eluted with n-hexane-acetone (19:1-14:6), and $CHCl_3$-MeOH (1:1) to give nine fractions (Fr. 1-9). Fraction 2 was chromatographed on silica gel to give compound 1 (8.7 mg). Fraction 4 was chromatographed on normal and reversed phase silica gel to give compound 2 (13.6 mg). Fraction 5 was chromatographed on silica gel eluted with n-hexane-acetone (8:2) to give ergosterol peroxide (35.8 mg). Fraction 6 gave compound 3 (14.6 mg) by combination of normal and reversed phase silica gel column chromatography. Fraction 7 yielded a mixture of compounds 4 and 5 (4:1) by column chromatography. The mixture of compounds 4 and 5 were subsequently separated by preparative HPLC [column: Tosoh TSK-gel ODS-80T$_M$ (21.5×300 mm), mobile phase: CH$_3$OH—H$_2$O containing 0.1% TFA (70:30)].

3-Isobutyl-4-[4-(3-methyl-2-butenyloxy)phenyl]furan-2,5-dione (compound 1): yellow oil; UV (MeOH) $\lambda_{max}$ (log ε) 227 (4.1), 258 (3.9), 275 (3.8), 355 (3.4) nm; IR (CHCl$_3$) $v_{max}$ 1763 cm$^{-1}$; $^1$H-NMR Table 1; $^{13}$C-NMR Table 2; EIMS m/z 314 [M]$^+$ (100), 246 (100), 131 (100); HR-EIMS m/z 314.1523 (Calcd for C$_{19}$H$_{22}$O$_4$, 314.1518).

3-Isobutyl-4-[4-(3-methyl-2-butenyloxy)phenyl]-1H-pyrrole-2,5-dione (2): yellow needles (n-hexane-AcOEt); mp 110-111° C.; UV (MeOH) $\lambda_{max}$ (log ε) 230 (4.3), 272 (3.5), 355 (3.7) nm; IR (CHCl$_3$) $v_{max}$ 1724 cm$^{-1}$; $^1$H-NMR Table 1; $^{13}$C-NMR Table 2; EIMS m/z 313 [M]$^+$ (8), 245 (100), 203 (77), 131 (28); HR-EIMS m/z 313.1681 (Calcd for C$_{19}$H$_{23}$NO$_3$, 313.1678).

X-Ray Crystallography of Compound 2:

Yellow needles were obtained by crystallization from n-hexane-AcOEt and selected for data collection. Crystal data: C$_{19}$H$_{23}$NO$_3$; M$_r$=313.40; dimensions 0.15×0.02×0.02 mm; triclinic, space group P1 (#2), a=6.3505(5) Å, b=12.205(1) Å, c=12.560(2) Å, α=64.623(7)°, β=75.358(4)°, γ=84.681(5)°, V=850.9(2) Å$^3$, Z=2, D$_{calc}$=1.223 g/cm$^3$, μ(MoKα)=0.82 cm$^{-1}$, F$_{000}$=336.00. Measurement was made on a Rigaku RAXIS-RAPID Imaging Plate diffractometer with graphite monochromated Mo—Kα (λ=0.71069 Å) radiation at 93 K.

Of the 8950 reflections that were collected, 4745 were unique (R$_{int}$=0.108); equivalent reflections were merged. The crystal structure was solved by direct methods (SHELXS86) and refined by full-matrix least-squares. The non-hydrogen atoms were refined anisotropically. Hydrogen atoms were included but not refined. The final indices were R=0.074, R$_w$=0.099, with GOF (Guest Observer Facility)=1.06. The maximum and minimum peaks on the final difference Fourier map corresponded to 0.83 and −0.89 e$^-$/Å$^3$, respectively.

3-Isobutyl-4-[4-(3-methyl-2-butenyloxy)phenyl]-1H-pyrrol-1-ol-2,5-dione (compound 3): yellow oil; UV (MeOH) $\lambda_{max}$ (log ε): 232.5 (4.3), 296 (3.7), 374 (3.7) nm; IR (CHCl$_3$) $v_{max}$ 1717 cm$^{-1}$; $^1$H-NMR Table 1; $^{13}$C-NMR Table 2; EIMS m/z 329 [M]$^+$ (12), 261 (100), 131 (50); HR-EIMS m/z: 329.1637 (Calcd for C$_{19}$H$_{23}$NO$_4$, 329.1627).

3R*,4S*-1-Hydroxy-3-isobutyl-4-[4-(3-methyl-2-butenyloxy)phenyl]pyrrolidine-2,5-dione (4): colorless oil; [α]$_D^{23}$+2.5° (c 0.2, MeOH); UV (MeOH) $\lambda_{max}$ (log ε): 225 (4.3), 275 (3.3), 283 (3.2) nm; IR (CHCl$_3$) $v_{max}$ 1715 cm$^{-1}$; $^1$H-NMR Table 1; $^{13}$C-NMR Table 2; EIMS m/z 331 [M]$^+$ (2), 263 (67), 207 (66), 191 (30), 179 (40), 133 (64), 69 (100); HR-EIMS m/z 331.1747 (Calcd for C$_{19}$H$_{25}$NO$_4$, 331.1783).

3R*,4R*-1-Hydroxy-3-isobutyl-4-[4-(3-methyl-2-butenyloxy) phenyl]pyrrolidine-2,5-dione (5): colorless oil; [α]$_D^{23}$+3.0° (c 0.2, MeOH); UV (MeOH) $\lambda_{max}$ (log ε): 227 (4.3), 275 (3.4), 283 (3.3) nm; IR (CHCl$_3$) $v_{max}$ 1715 cm$^{-1}$; $^1$H-NMR Table 1; $^{13}$C-NMR Table 2; EIMS m/z 331 [M]$^+$ (1), 263 (45), 207 (50), 191 (75), 179 (30), 133 (100), 69 (92); HR-EIMS m/z 331.1766 (Calcd for C$_{19}$H$_{25}$NO$_4$, 331.1783).

Results and Discussion

The CHCl$_3$ extract of the mycelium of *Antrodia camphorata* was repeatedly chromatographed on normal and reversed phase silica gel to afford five new maleic and succinic acid derivatives (compounds 1-5) together with ergosterol peroxide.

TABLE 1

Table 1. $^1$H-NMR Spectral Data of Compounds 1-5 (δ ppm, J = Hz) (500 MHz, CDCl$_3$)

| H | 1 | 2 | 3 | 4 | 5 |
|---|---|---|---|---|---|
| 3 | — | — | — | 2.87 (1H, m) | 3.08 (1H, m) |
| 4 | — | — | — | 3.52 (1H, d, J = 4.0) | 4.07 (1H, d, J = 8.0) |
| 1' | 2.59 (2H, d, J = 7.0) | 2.51 (2H, d, J = 7.0) | 2.50 (2H, d, J = 7.0) | 1.51 (1H, m) 1.72~1.84 (1H) | 1.02 (1H, m) 1.42~1.48 (1H) |
| 2' | 2.12 (1H, sep, J = 7.0) | 2.06 (1H, sep, J = 7.0) | 2.05 (1H, sep, J = 7.0) | 1.72~1.84 (1H) | 1.42~1.48 (1H) |
| 3' | 0.94 (6H, d, J = 7.0) | 0.90 (6H, d, J = 7.0) | 0.88 (6H, d, J = 7.0) | 0.70 (3H, d, J = 6.5) | 0.66 (3H, d, J = 6.5) |
| 4' | | | | 0.89 (3H, d, J = 6.5) | 0.80 (3H, d, J = 6.5) |
| 2", 6" | 7.50 (2H, d, J = 9.0) | 7.50 (2H, d, J = 9.0) | 7.50 (2H, d, J = 9.0) | 7.07 (2H, d, J = 8.5) | 6.96 (2H, d, J = 9.0) |
| 3", 5" | 7.02 (2H, d, J = 9.0) | 6.95 (2H, d, J = 9.0) | 6.98 (2H, d, J = 9.0) | 6.87 (2H, d, J = 8.5) | 6.84 (2H, d, J = 9.0) |
| 1''' | 4.57 (2H, d, J = 6.6) | 4.56 (2H, d, J = 6.5) | 4.55 (2H, d, J = 6.9) | 4.47 (2H, d, J = 6.5) | 4.47 (2H, d, J = 6.5) |
| 2''' | 5.50 (1H, brt, J = 6.6) | 5.50 (1H, brt, J = 6.5) | 5.49 (1H, brt, J = 6.9) | 5.47 (1H, brt, J = 6.5) | 5.47 (1H, brt, J = 6.5) |
| 4''' | 1.81 (3H, s) | 1.81 (3H, s) | 1.81 (3H, s) | 1.79 (3H, s) | 1.79 (3H, s) |
| 5''' | 1.76 (3H, s) | 1.76 (3H, s) | 1.76 (3H, s) | 1.73 (3H, s) | 1.73 (3H, s) |

TABLE 2

$^{13}$C-NMR Spectral Data for Compound 1-5
(δ ppm) (125 MHz, CDCl$_3$)

| C | 1 | 2 | 3 | 4 | 5 |
|---|---|---|---|---|---|
| 2 | 166.4 (s) | 171.7 (s) | 168.8 (s) | 174.8 (s) | 175.1 (s) |
| 3 | 139.8 (s) | 138.8 (s)$^{a)}$ | 135.9 (s)$^{a)}$ | 44.6 (d) | 40.3 (d) |
| 4 | 140.2 (s) | 139.2 (s)$^{a)}$ | 136.0 (s)$^{a)}$ | 49.8 (d) | 47.5 (d) |
| 5 | 165.4 (s) | 171.1 (s) | 168.1 (s) | 173.2 (s) | 173.6 (s) |
| 1' | 33.6 (t) | 32.8 (t) | 33.2 (t) | 40.4 (t) | 35.3 (t) |
| 2' | 27.9 (d) | 28.1 (d) | 28.4 (d) | 25.3 (d) | 25.2 (d) |
| 3' | 22.7 (q) | 22.7 (q) | 23.0 (q) | 21.3 (q) | 21.8 (q) |
| 4' | | | | 23.0 (q) | 22.4 (q) |
| 1" | 119.9 (s) | 121.2 (s) | 120.8 (s) | 127.9 (s) | 125.1 (s) |
| 2", 6" | 131.1 (d) | 130.9 (d) | 131.0 (d) | 128.8 (d) | 130.2 (d) |
| 3", 5" | 115.1 (d) | 114.9 (d) | 115.0 (d) | 115.4 (d) | 115.0 (d) |
| 4" | 160.9 (s) | 160.1 (s) | 160.2 (s) | 158.7 (s) | 158.7 (s) |
| 1''' | 65.0 (t) | 64.9 (t) | 65.1 (t) | 64.1 (t) | 64.8 (t) |
| 2''' | 118.7 (d) | 119.3 (d) | 119.2 (d) | 119.4 (d) | 119.3 (d) |
| 3''' | 139.1 (s) | 138.6 (s)$^{a)}$ | 138.9 (s) | 138.3 (s) | 138.4 (s) |
| 4''' | 25.2 (q) | 25.8 (q) | 26.1 (q) | 25.8 (q) | 25.8 (q) |
| 5''' | 18.2 (q) | 18.2 (q) | 18.5 (q) | 18.1 (q) | 18.2 (q) |

$^{a)}$Assignments may be interchangeable.

The structures of the new compounds were determined as follows: The molecular formula of compound 1 was assigned as C$_{19}$H$_{22}$O$_4$ by HR-EIMS. The IR spectrum revealed carbonyl absorption of acid anhydride at 1763 cm$^{-1}$. The $^1$H-NMR spectrum of compound 1 was similar to that of compound 2, and showed the presence of an isobutyl moiety, a 3-methyl-2-butenyloxy moiety, and a para-substituted benzene ring. From the HMBC spectrum, compound 1 was demonstrated to have the same partial structure to compound 2 (FIG. 1), in which the presence of a maleic anhydride group was deduced on the basis of the molecular formula compound 1 was consequently determined as 3-isobutyl-4-[4-(3-methyl-2-butenyloxy)phenyl]furan-2,5-dione.

Compound 2 gave yellow needles, mp 110-111° C., and the molecular formula C$_{19}$H$_{23}$NO$_3$ was assigned by HR-EIMS. The IR spectrum showed an imide carbonyl absorption at 1724 cm$^{-1}$. The $^{13}$C-NMR spectrum showed signals of four methyl carbons, two methylene carbons, and one methine carbon in the aliphatic region, as well as one benzene ring, one olefinic group and two carbonyl carbons. The $^1$H-NMR spectrum showed the presence of an isobutyl moiety at δ 0.90, 2.06, and 2.51, a 3-methyl-2-butenyloxy moiety at δ 1.76, 1.81, 4.56, and 5.50, and a para-substituted benzene moiety at δ 6.95 and 7.50, which was further supported by $^1$H-$^1$H COSY (cooler synchrotron) and HMQC (heteronuclear multiple quantum coherence) experiments. Long-range correlations were observed by HMBC as shown in FIG. 1. On the basis of the molecular formula and the $^{13}$C-NMR spectrum, this compound was deduced to contain further CHNO atoms, including one more carbonyl carbon. Thus, this ambiguous part was speculated to be a maleimide group. This structure was then established to be 3-isobutyl-4-[4-(3-methyl-2-butenyloxy)phenyl]-1H-pyrrole-2,5-dione by X-ray analysis.

The molecular formula of compound 3 was assigned as C$_{19}$H$_{23}$NO$_4$ by HR-EIMS. The IR spectrum showed carbonyl absorption at 1717 cm$^{-1}$, assignable to a hydroxy imide. The $^1$H- and $^{13}$C-NMR spectra were also similar to those of compounds 1 and 2, and showed the presence of an isobutyl moiety, a 3-methyl-2-butenyloxy moiety, and apara-substituted benzene ring. In the HMBC experiment, compound 3 was shown to have the same partial structure as compound 2 (FIG. 1). Compound 3 contains one more oxygen atom than compound 2, therefore, this compound was determined to be (3-isobutyl-4-[4-(3-methyl-2-butenyloxy)phenyl-1H-pyrrol-1-ol-2,5-dione.

Compounds 4 and 5 had the same R$_f$ values and the same molecular formula by HR-EIMS (C$_{19}$H$_{25}$NO$_4$, found 331.1747 and 331.1766, respectively), however, they could be separated by preparative HPLC. The IR spectrum of both compounds showed a hydroxy imide carbonyl absorption at 1715 cm$^{-1}$. In the $^1$H- and $^{13}$C-NMR spectra, both compounds showed the presence of an isobutyl moiety, a 3-methyl-2-butenyloxy moiety, and a para-substituted benzene ring, but the isobutyl methylene protons displayed a multiplet and not a doublet as for compounds 1-3. The $^1$H-$^1$H COSY spectrum indicated that this methylene group is attached to a —CH—CH— unit. The $^{13}$C-NMR spectra of compounds 4 and 5 exhibited two additional sp$^3$ carbon signals, replacing two sp$^2$ carbon signals observed for compounds 1-3. Therefore, compounds 4 and 5 were not N-hydroxy maleimides, but rather N-hydroxy succinimides, with stereocenters at positions C-3 and C-4 in the succinimide ring. Compounds 4 and 5 were determined to be trans and cis isomers, respectively, from the coupling constant between H-3 and H-4 (4.0 and 8.0 Hz for compounds 4 and 5, respectively). No NOE was observed between H-3 and H-4 in the NOESY (Nuclear Overhauser Effect Spectroscopy) spectrum of compound 4, while appreciable NOE was observed in that of compound 5. The optical rotations of compounds 4 and 5 showed +2.5° and +3.0°, respectively, while their CD spectra showed no Cotton effects at any wave length, suggesting that both compounds 4 and 5 are racemic mixtures. Resolution of these racemic mixtures by HPLC using a chiral column with several solvent systems was unsuccessful. At present, we cannot definitely conclude whether these compounds are optically active compounds or racemic mixtures. Thus, their relative structures were determined as 3R*,4S*- and 3R*,4R*-1-hydroxy-3-isobutyl-4-[4-(3-methyl-2-butenyloxy)phenyl]pyrrolidine-2,5-dione, respectively.

Example 2

Compound 2 as ROS Scavenger and Down Regulated TGF-β Mediated Inflammation and Fibrosis Transfection and Dual-luciferase Assay:

HSC-T6 cells (1.5×10$^5$) were plated in each well of six-well plates. Transient transfection was carried out by the calcium phosphate precipitation method. The plasmid pRL-TK was cotransfected to normalize the transfection efficiency. After 12 h of transfection, the medium was changed, and the cells were incubated at 37° C. for 24 or 48 h. The cells were washed in phosphate-buffered saline (137 mM sodium chloride, 2.7 mM potassium chloride, 10 mM dibasic sodium phosphate, and 2 mM monobasic potassium phosphate) and the lysates were prepared by scraping the cells from plates in the presence of 1× passive lysis buffer (Promega). Luciferase assays were performed by using Dual-Luciferase Assay System (Promega) and a Sirius luminometer (Berthold Detection System, Pforzheim, Germany).

Preparation of Nuclear Extracts:

HSC-T6 cells were plated onto 6- or 10-cm cultured dishes and incubated for 2 days. The cells were washed with 2 ml of phosphate-buffered saline and collected in 1 ml of phosphate-buffered saline. The cells were centrifuged at 2,000×g for 2 min, and the supernatant was discarded. The cell pellet was incubated in 400 μl of buffer A (10 mM HEPES (pH 7.9), 1.5 mM magnesium chloride, 10 mM potassium chloride, 0.5 mM phenylmethylsulfonyl fluoride, 0.5 mM dithiothreitol, 2 g/ml leupeptin, 10 g/ml aprotinin, 50 mM sodium fluoride, and 1 mM sodium orthovanadate) on ice for 10 min and then gently shaken for 10 s. The pellet of the crude nuclei was collected by centrifugation at 12,000×g for 10 s. The pellet was resuspended in 100 l of buffer C (20 mM HEPES (pH 7.9), 25% glycerol, 420 mM sodium chloride, 1.5 mM magnesium chloride, 0.2 mM EDTA, 0.5 mM phenylmethylsulfonyl fluoride, 0.5 mM dithiothreitol, 2 g/ml leupeptin, 10 g/ml aprotinin, 50 mM sodium fluoride, and 1 mM sodium orthovanadate) by vortex for 15 s, and then incubated on ice for 20 min. After centrifugation at 12,000×g for 2 min, the supernatant containing the nuclear proteins was collected, quantified with BCA Protein Assay Reagent (Pierce), and stored at −70° C. in aliquots.

Figure 2:
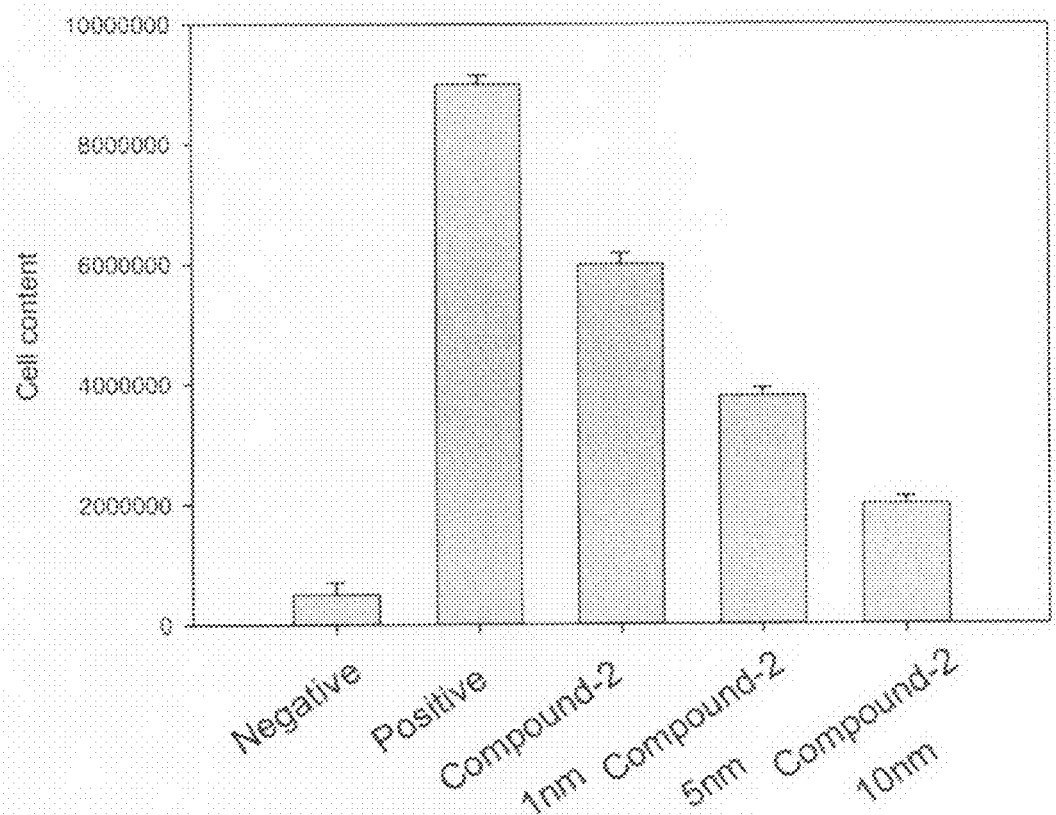
FIG. 2 shows the ROS assay results.
Figure 4:
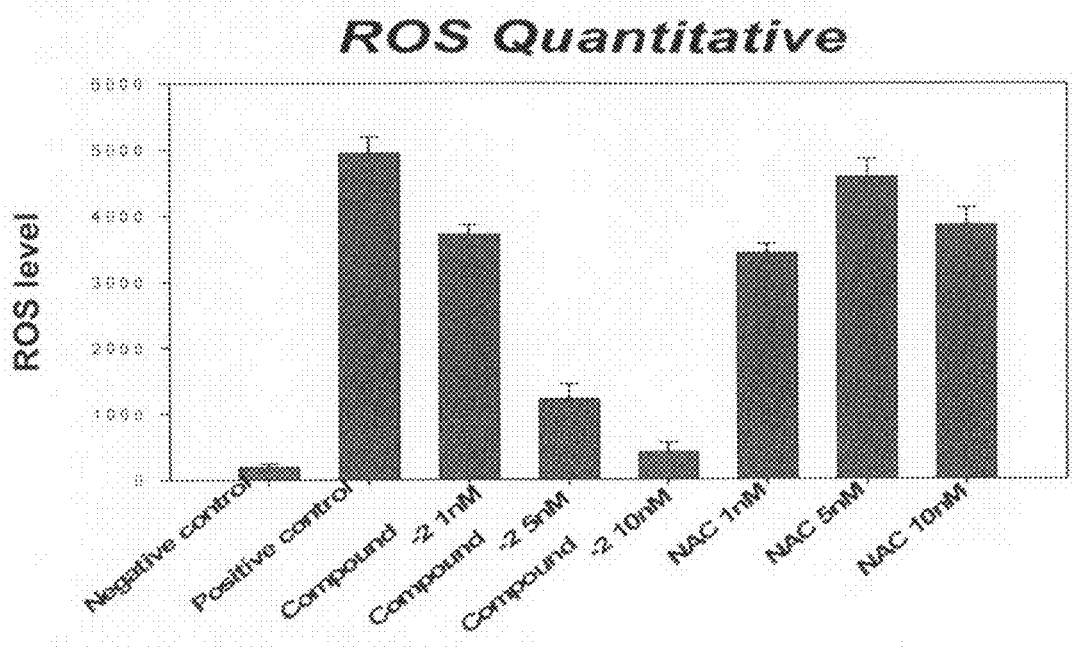
FIG. 4 shows the ROS quantitative results.

Measurement of Intracellular ROS:

For visualization and analysis of intracellular ROS, the oxidation-sensitive probe DCFH-DA was used, as previously described. To analyze the net intracellular generation of ROS by flow cytometry, cells were detached by trypsinization after incubation in the absence or presence of the different factors. The cellular fluorescence intensity was measured after 30 min incubation with 5 mM DCFH-DA, by using the same flow cytometer described above. Propidium iodide (0.005%) was used to detect dead cells. For each analysis, 10,000 events were recorded. For confocal microscopy analysis, after incubation of cells in the absence or presence of the different factors, they were washed twice with PBS and the cellular fluorescence intensity was visualized after 30 min of incubation with 5 mM DCFH-DA by using the same confocal microscopy described above. The analysis results were illustrated in FIGS. 2-4.

Figure 5:
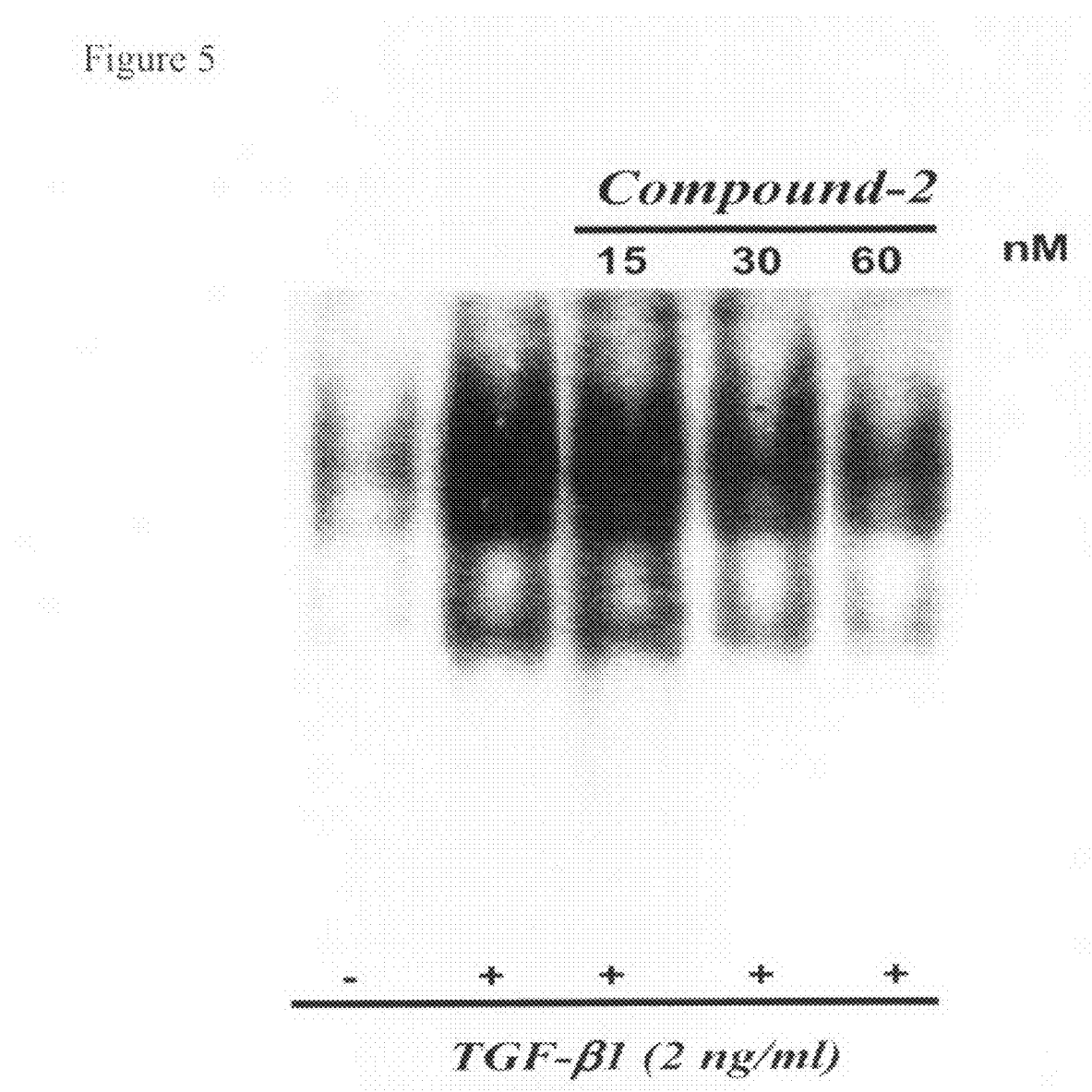
FIG. 5 shows test results of gel electrophoretic mobility shift assays.

Gel Electrophoretic Mobility Shift Assays (EMSA):

The EMSA used the following oligonucleotides: consensus Sp1 (f), 5'-GTT GCG GGG CGG GGC CGA GTG-3'; consensus Sp1 (r), 3'-AAC GCC CCG CCC CGG CTC ACG-5'. 30 pmol of each of the forward and reverse oligonucleotides placed in a volume of 23 μl of 1× Klenow (DNA polymerase) buffer were heated at 94° C. for 2 min and annealed at room temperature for 30 min. The annealed double-stranded oligonucleotides were end-labeled by a fill-in reaction using DNA polymerase (Klenow)(Promega). One unit of the DNA polymerase (Klenow) and 40 Ci of (−32P) dCTP (PerkinElmer Life Sciences) were added into the annealed oligonucleotides and the mixture was incubated at 30° C. for 15 min. The labeled oligonucleotides were purified by Sephadex G-50 columns (Amersham Biosciences). Cold double-stranded oligonucleotides were used as competitors. The DNA binding reaction was conducted at 4° C. for 30 min in a mixture containing 3 g of nuclear extract, 10 mM Tris-Cl (pH 7.5), 50 mM sodium chloride, 0.5 mM dithiothreitol, 0.5 mM EDTA, 1 mM magnesium chloride, 4% glycerol, 0.05 g poly(dI-dC)•poly(dI-dC) (Amersham Biosciences) and 2×10$^4$ cpm of 32P-labeled double-stranded oligonucleotides. In supershift assays, antibodies were incubated with the reaction mixture at 4° C. for 30 min before the addition of the SP-1 probes. Samples were analyzed on a 4% polyacrylamide gel (acrylamide/bisacrylamide 29:1 in 0.5×Tris borate-EDTA buffer) at 10 V/cm for 2.5 h. The gel was dried and analyzed by autoradiography. The test results were illustrated in FIG. 5.

Figure 6:
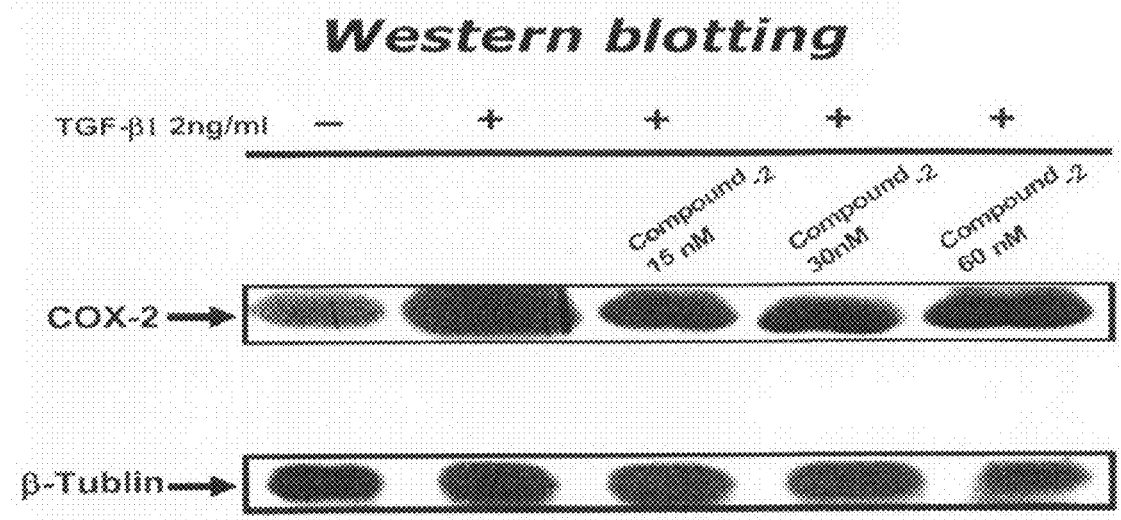
FIG. 6 shows test results of SDS-PAGE and Western blotting assays.
Figure 7:
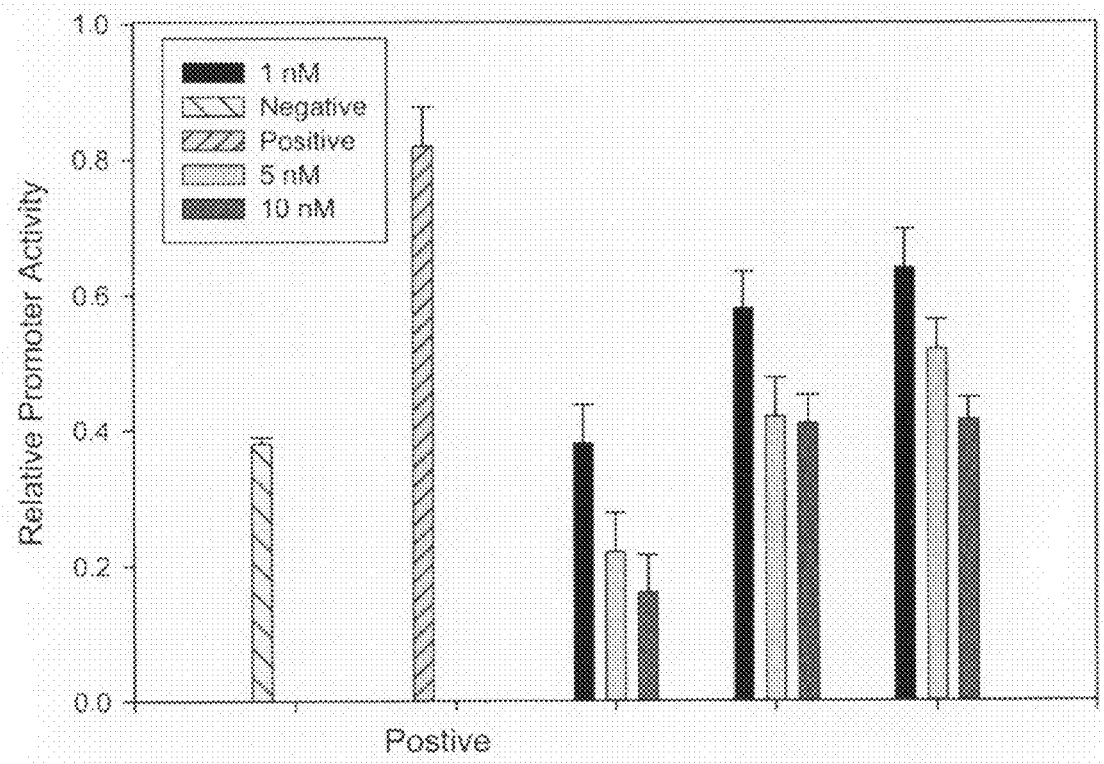
FIG. 7 shows test results of COX-2 promoter assay.

Western Blot Analysis:

Liver samples (0.5 g) were lysed (Reporter lysis buffer, Promega, Madison, Wis., USA), the protein were boiled in Laemmli's sample buffer and samples were subjected to 10% SDSPAGE followed by western immunoblotting. Anti-cyclooxygenase was used as the first antibody, followed by secondary HRP-conjugated goat anti-rabbit antibodies (Santa Cruz). Immunoreactive bands were detected using the enhanced chemiluminescence (ECL) reagent using Super-Signal West Pico Chemiluminescent Substrate (Pierce, Rockford, Ill., USA). The light emitted by the chemical reaction was detected by exposure to Hyperfilm ECL (Amersham Biosciences, Uppsala, Sweden). The analysis results were illustrated in FIG. 6.

Method and Material

Cell Model:

HSC-T6 fibrosis was induced TGF-β 2 ng/ml in MEM medium these cells by three experimental procedures to gauge how compound 2 influences ROS, collagen 1 A2 COX-2 promoter assay, and stains alpha-smooth muscle actin, smad4, smad3.

The influences of hepacin on mice-derived once-activated HSC-T6 line were studied. HSC-T6 was directed to with a focus on the collagen alpha2 (I) (COL1A2) promoter expression. Plasmid containing 353 nt length of COL1A2 promoter linked to firefly luciferase gene and its various 5'-deletions were transiently transfected to HSC-T6. The luciferase activity was determined with or without 10, 5, 1 nM of hepacin in the absence or presence of 2 ng/ml of transforming growth factor TGF-β. The effects of hepacin on generation of intracellular reactive oxygen species (ROS) in HSC-T6 were also analyzed.

Figure 8:
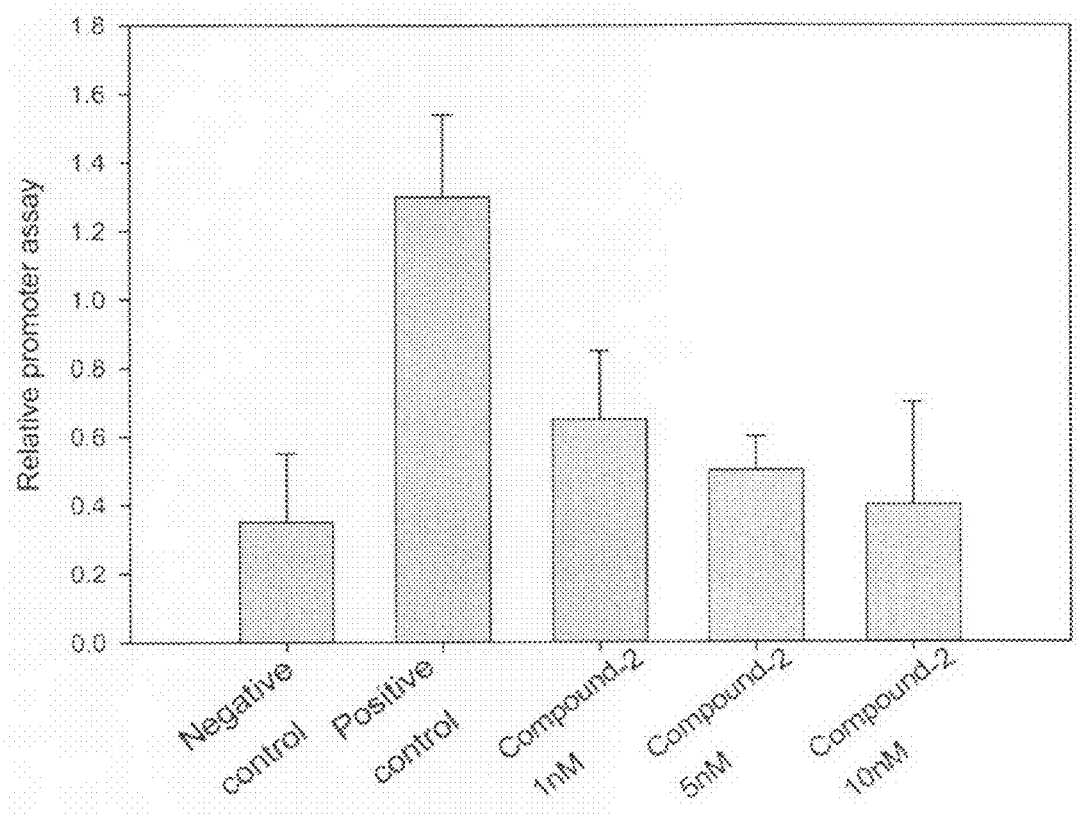
FIG. 8 shows test result of Col1A2 promoter assay.

As shown in FIG. 8, HSC-T6 significantly ($P<0.05$) suppressed the COL1A2 promoter expression in the absence or presence of TGF-β.

Figure 9:
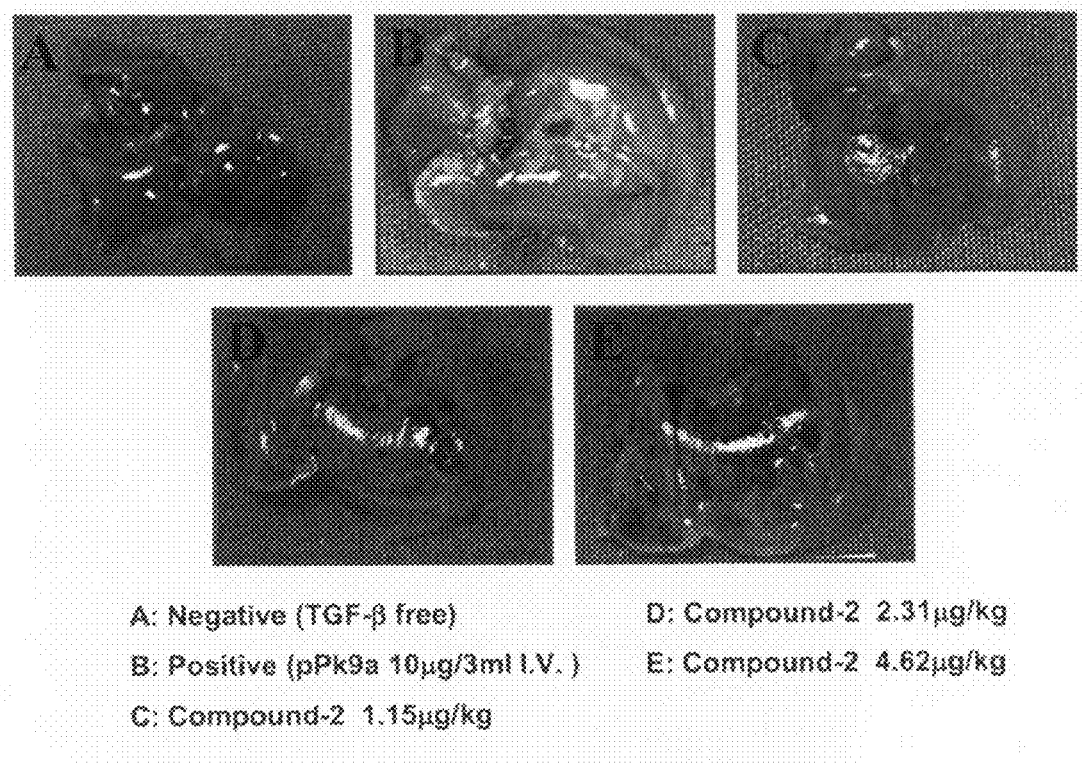
FIG. 9 shows the influence of compound 2 on mouse liver collagen. A: negative (TGF-β free), B: positive (pPk9a 10 μg/3 ml i.v.), C: compound-2 1.15 μg/kg, D: compound-2 2.31 μg/kg, and E: compound-2 4.62 μg/kg.
Figure 10:
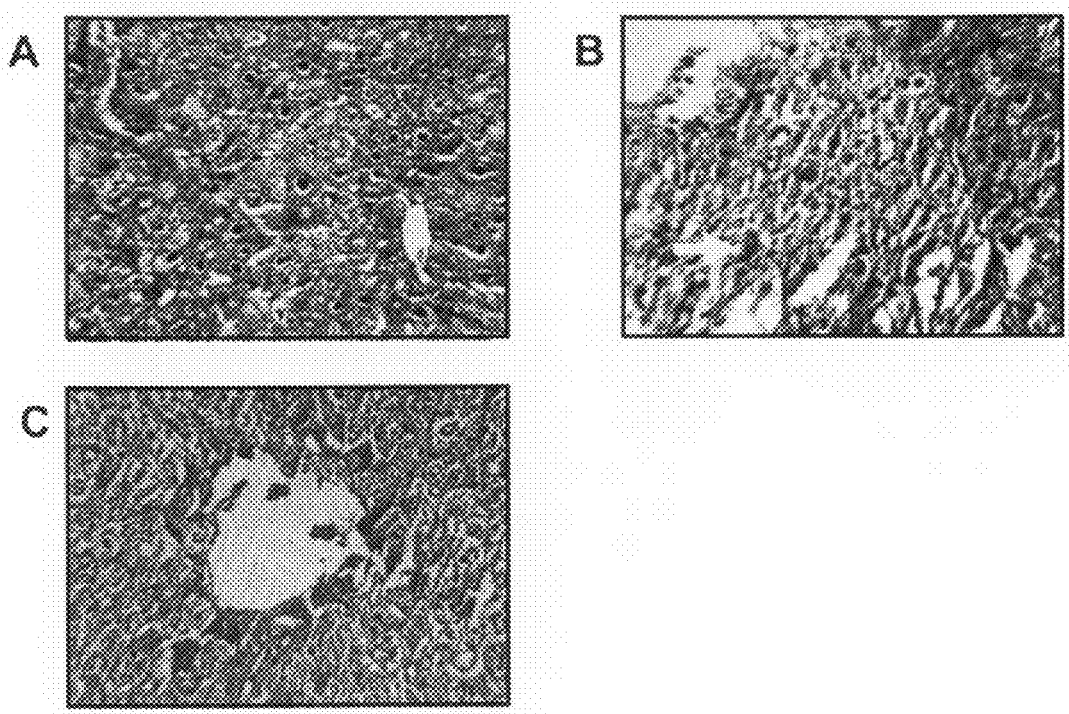
FIG. 10 shows the Masson's trichrome stain for collagen. A: negative (TGF-β free), B: positive (TGF-β 2 ng/ml), and C: compound-2 1 μg/kg. Collagen fiber accumulation in the sinusoidal wall is blue-stained (arrows). The original magnification is ×200.

Animal Model:

Liver fibrosis was induced in these animals by hydrodynamic method; within 7 second injection mouse tail vein 3 ml ringer' solution containing 10 μg plasmid of pPK9a which would be generated TGF-β induced by 100 uM zinc sulfate in water unlimited feed to gauge how compound 2 influences liver collagen. The test results were illustrated in FIGS. 9 and 10.

Conclusion

Given the above tests, it demonstrated that the compounds of the invention could be regarded as a strong antioxidants to scavenge ROS and down regulated TGF-β mediated inflammation and fibrosis Example 3

Inhibition of Nitric Oxide by Extract from Example 1
Cell Subculture Steps
Manipulation RAW264.7 cells were incubated at 37° C. in a 5% $CO_2$ and 90% relative humidity incubator in DMEM (Dulbucco's Modified Eagle Medium) containing 2 mM L-glutamine, 100 U/ml penicillin G, 100 μg/ml streptomycin sulfate, 10% fetal bovine serum (FBS) with growing 80~90% confluence, then passaged by different test purposes.

Assay and Analysis of Nitrite
Material and Reagent
(1) Griess reagent solution (1% sulfanilamide, 0.1% naphthlethylenediamine dihydrochloride in 2.5% phosphoric acid).
(2) Sodium nitrite Protocol
(1) Cells were treated with drugs in appropriate dosage and incubated at 37° C. in a 5% $CO_2$ incubator.

(2) After treating cells with various dosages over specific time, they were taken out from the incubator and transferred 100 μl medium into a 96 well plate, respectively.

(3) A calibration curve was made by sodium nitrite, and each well was added with 100 μl by serial dilution.

(4) Each sample and well was further added with 100 μl Griess reagent solution over 10 minutes.

(5) Absorbance was read at 570 nm using an ELISA reader directly and compared with calibration curve to get the concentration of nitrite in the samples.

Figure 11:
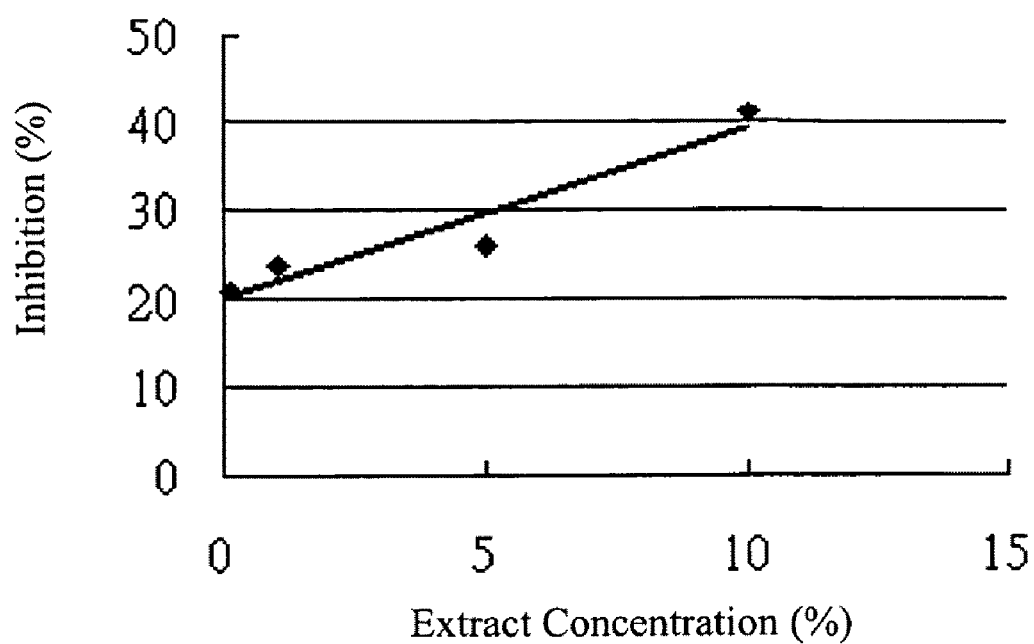
FIG. 11 shows the effect of the extract on nitric oxide inhibition.

The test results were illustrated in FIG. 11. Given the above tests, it demonstrated that the extract of *Antrodia camphorata* actually inhibited nitric oxide activity. The inhibition of nitric oxide activity was increasing depended on the higher concentration of the extract.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The cell lines, embryos, animals, and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

What is claimed is:

1. A method of treating fibrosis in a mammal, wherein the fibrosis is mediated by TGF-β, the method comprising administering to the mammal a compound having the formula

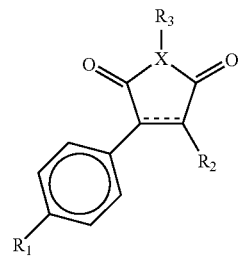

wherein
  X is N or O;

$R_1$ is H, hydroxyl, $C_{1-10}$ alkyloxy, $C_{2-10}$ alkenyloxy, which is unsubstituted or substituted with $C_{1-6}$ alkyl, or $C_{2-10}$ alkynyloxy;

$R_2$ is H, hydroxyl, $C_{1-10}$ alkyl, $C_{2-10}$ alkenyl or $C_{2-10}$ alkynyl;

$R_3$ is $C_{1-10}$ alkyl, $C_{2-10}$ alkenyl or $C_{2-10}$ alkynyl;

----- denotes a single or double bond;

provided that if X is O, $R_3$ is absent;

if ----- denotes a single bond, the compound has the formula:

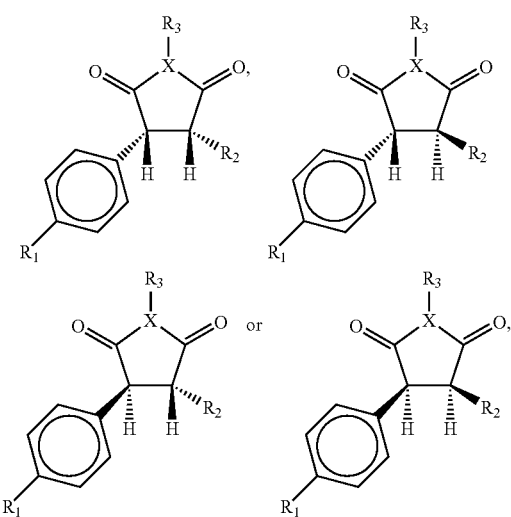

or a tautomer, stereoisomer, or pharmaceutically acceptable salt thereof.

2. The method of claim 1, wherein $R_1$ is $C_{2-6}$ alkenyloxy or $C_{2-6}$ alkynyloxy.

3. The method of claim 2, wherein $C_{2-6}$ alkenyloxy is substituted with methyl.

4. The method of claim 1, wherein $R_2$ is isobutyl.

5. The method of claim 1, wherein the mammal is a human.

6. The method of claim 1, wherein the fibrosis is associated with a disease state selected from the group consisting of diabetic nephropathy, liver cirrhosis, idiopathic pulmonary fibrosis, rheumatoid arthritis, fibrosarcomas, arteriosclerosis, and scleroderma.

7. A method of downregulating TGF-β in a mammal, comprising administering to the mammal a compound having the formula

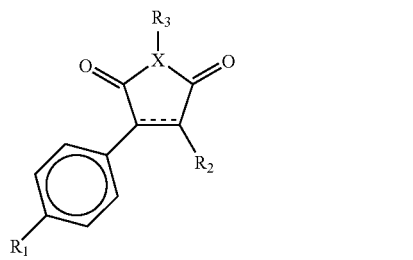

wherein

X is N or O;

$R_1$ is H, hydroxyl, $C_{1-10}$ alkyloxy, $C_{2-10}$ alkenyloxy, which is unsubstituted or substituted with $C_{1-6}$ alkyl, or $C_{2-10}$ alkynyloxy;

$R_2$ is H, hydroxyl, $C_{1-10}$ alkyl, $C_{2-10}$ alkenyl or $C_{2-10}$ alkynyl;

$R_3$ is $C_{1-10}$ alkyl, $C_{2-10}$ alkenyl or $C_{2-10}$ alkynyl;

----- denotes a single or double bond;

provided that if X is O, $R_3$ is absent;

if ----- denotes a single bond, the compound has the formula:

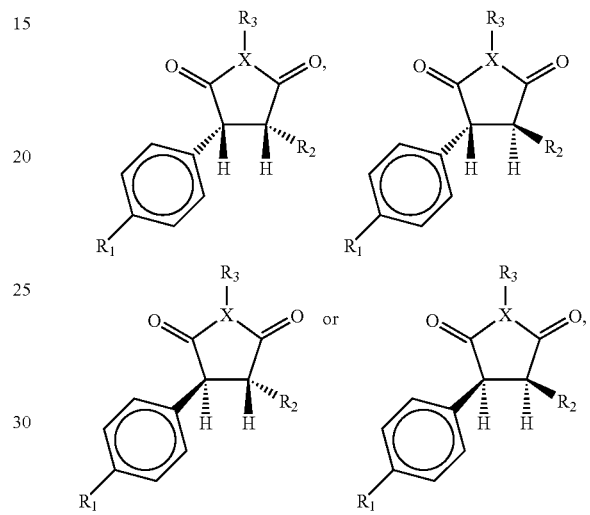

or a tautomer, stereoisomer, or pharmaceutically acceptable salt thereof.

8. The method of claim 7, wherein $R_1$ is $C_{2-6}$ alkenyloxy or $C_{2-6}$ alkynyloxy.

9. The method of claim 8, wherein $C_{2-6}$ alkenyloxy is substituted with methyl.

10. The method of claim 1, wherein $R_2$ is isobutyl.

11. The method of claim 1, wherein the mammal is a human.

12. The method of claim 7, wherein the TGF-β is associated with a disease state selected from the group consisting of diabetic nephropathy, liver cirrhosis, idiopathic pulmonary fibrosis, rheumatoid arthritis, fibrosarcomas, arteriosclerosis, and scleroderma.

13. A method of treating fibrosis in a mammal, wherein the fibrosis is mediated by TGF-β, the method comprising administering to the mammal a compound having the formula

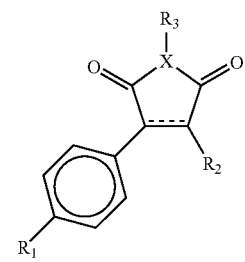

wherein

X is N or O;

$R_1$ is H, hydroxyl, $C_{1-10}$ alkyloxy, $C_{2-10}$ alkenyloxy, which is unsubstituted or substituted with $C_{1-6}$, or $C_{2-10}$ alkynyloxy;

$R_2$ is H, hydroxyl, $C_{1-10}$ alkyl, $C_{2-10}$ alkenyl or $C_{2-10}$ alkynyl;

$R_3$ is absent, H, hydroxyl or $C_{1-10}$ alkyl, $C_{2-10}$ alkenyl or $C_{2-10}$ alkynyl;

----- denotes a single or double bond;

provided that if X is O, $R_3$ is absent;

if ----- denotes a single bond, the compound has the formula:

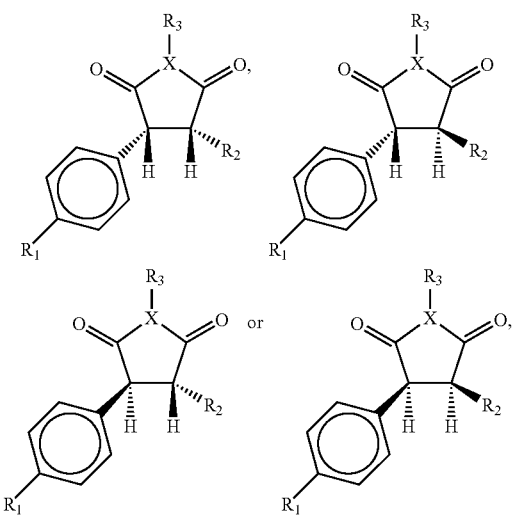

or a tautomer, stereoisomer, or pharmaceutically acceptable salt thereof.

14. The method of claim 13, wherein $R_1$ is $C_{2-6}$ alkenyloxy or $C_{2-6}$ alkynyloxy.

15. The method of claim 14, wherein $C_{2-6}$ alkenyloxy is substituted with methyl.

16. The method of claim 13, wherein $R_2$ is isobutyl.

17. The method of claim 13, wherein the mammal is a human.

18. The method of claim 13, wherein the fibrosis is associated with a disease state selected from the group consisting of diabetic nephropathy, liver cirrhosis, idiopathic pulmonary fibrosis, rheumatoid arthritis, fibrosarcomas, arteriosclerosis, and scleroderma.

19. A method of downregulating TGF-β in a mammal, comprising administering to the mammal a compound having the formula

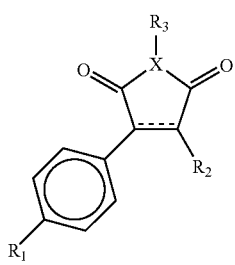

wherein

X is N or O;

$R_1$ is H, hydroxyl, $C_{1-10}$ alkyloxy, $C_{2-10}$ alkenyloxy, which is unsubstituted or substituted with $C_{1-6}$ alkyl, or $C_{2-10}$ alkynyloxy;

$R_2$ is H, hydroxyl, $C_{1-10}$ alkyl, $C_{2-10}$ alkenyl or $C_{2-10}$ alkynyl;

$R_3$ is absent, H, hydroxyl or $C_{1-10}$ alkyl, $C_{2-10}$ alkenyl or $C_{2-10}$ alkynyl;

----- denotes a single or double bond;

provided that if X is O, $R_3$ is absent;

if ----- denotes a single bond, the compound has the formula:

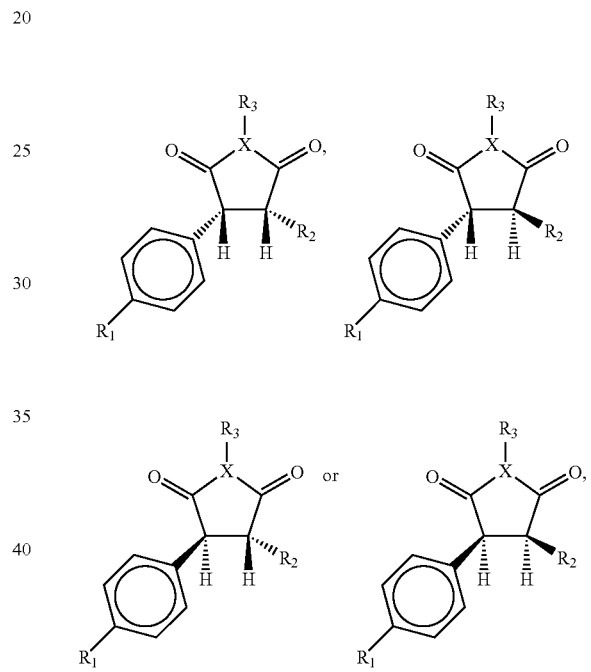

or a tautomer, stereoisomer, or pharmaceutically acceptable salt thereof.

20. The method of claim 19, wherein $R_1$ is $C_{2-6}$ alkenyloxy or $C_{2-6}$ alkynyloxy.

21. The method of claim 20, wherein $C_{2-6}$ alkenyloxy is substituted with methyl.

22. The method of claim 19, wherein $R_2$ is isobutyl.

23. The method of claim 19, wherein the mammal is a human.

24. The method of claim 19, wherein the TGF-β is associated with a disease state selected from the group consisting of diabetic nephropathy, liver cirrhosis, idiopathic pulmonary fibrosis, rheumatoid arthritis, fibrosarcomas, arteriosclerosis, and scleroderma.

* * * * *

SEQUENCE LISTING

<160> NUMBER OF SEQ ID NOS: 2

<210> SEQ ID NO 1
<211> LENGTH: 21
<212> TYPE: DNA
<213> ORGANISM: Artificial
<220> FEATURE:
<223> OTHER INFORMATION: Consensus Sp1 (f)

<400> SEQUENCE: 1
gttgcggggc ggggccgagt g                                       21

<210> SEQ ID NO 2
<211> LENGTH: 21
<212> TYPE: DNA
<213> ORGANISM: Artificial
<220> FEATURE:
<223> OTHER INFORMATION: consensus Sp1 (r)

<400> SEQUENCE: 2
aacgccccgc cccggctcac g                                       21